(12) United States Patent
Mårin

(10) Patent No.: US 6,274,582 B1
(45) Date of Patent: Aug. 14, 2001

(54) PREPARATION FOR THE TREATMENT OF METABOLIC SYNDROME CONTAINING HUMAN GROWTH HORMONE IN COMBINATION WITH A CORTISOL SYNTHESIS INHIBITOR

(75) Inventor: Per Mårin, Göteborg (SE)

(73) Assignee: Cortendo AB, Vastra Frolunda (SE)

( * ) Notice: Subject to any disclaimer, the term of this patent is extended or adjusted under 35 U.S.C. 154(b) by 0 days.

(21) Appl. No.: 09/379,832

(22) Filed: Aug. 24, 1999

Related U.S. Application Data

(63) Continuation of application No. PCT/GB98/00574, filed on Feb. 24, 1998.

(30) Foreign Application Priority Data

Feb. 24, 1997 (SE) .................................................. 9700642

(51) Int. Cl.[7] ...................... A61K 31/495; A61K 31/415; A61K 38/00
(52) U.S. Cl. .......................... 514/254.1; 514/399; 514/12; 514/178; 514/179
(58) Field of Search .............................. 514/12, 178, 179, 514/254.1, 399

(56) References Cited

FOREIGN PATENT DOCUMENTS

WO9604912  2/1996 (WO).

OTHER PUBLICATIONS

Johannsson et al, J Clen Endicrin Metab 82 (3) 725–6 Abstract, Mar., 1997.*
Hew et al. (1996) *Endocrinology and Metabolism*: 3 (Suppl. A), 55–60.
Bengtsson et al. (1992) *Acta Paediatr Suppl. 383*: 62–65.
Marin, P. (1996) "Possible Biological Mechanisms in Testosterone Replacement Therapy" Neuroendocrine News 21(3):2.

* cited by examiner

Primary Examiner—Rebecca Cook
(74) Attorney, Agent, or Firm—Baker Botts

(57) ABSTRACT

Human growth hormone is used in combination with a cortisol synthesis inhibitor, in particular ketoconazole, for prevention or treatment of conditions related to Metabolis Syndrome (Neuroendocrine Syndrome). Administration can be supplemented by a sex hormone selected from testosterone and natural or synthetic estrogen. Also disclosed are corresponding pharmaceutical compositions.

18 Claims, No Drawings

PREPARATION FOR THE TREATMENT OF METABOLIC SYNDROME CONTAINING HUMAN GROWTH HORMONE IN COMBINATION WITH A CORTISOL SYNTHESIS INHIBITOR

This application is continuation of PCT/GB98/00574 filed Feb. 24, 1998.

The present invention relates to the prevention and treatment of Metabolic Syndrome. More particularly, the invention relates to medicaments, preparations and treatments comprising cortisol synthesis inhibitors and growth hormone for treating the conditions which comprise the Metabolic Syndrome.

In both men and women, visceral (intra-abdominal) fat accumulation is associated with an increased risk of the development of non-insulin dependent diabetes, myocardial infarction, stroke and other arteriosclerotic diseases and their associated risk factors, including insulin resistance, elevated blood lipids, glucose and hypertension. The clustering of these risk factors has been designated 'Metabolic Syndrome', also called 'Syndrome X', the 'Insulin Resistance Syndrome' or the 'Deadly Quartet'. This syndrome is also characterised by one or more endocrine disturbances and is therefore also called 'Neuro-endocrine Syndrome' (Marin, P. Neuroendocrine News, 21(3) 1996, 2). These disturbances include low serum levels of sex steroids (testosterone in men, and estrogens in women), signs of a decreased action of growth hormone, and an excessive secretion of cortisol. The latter has been shown clinically as a major causative process for the development of Metabolic Syndrome as demonstrated by successful treatment with the cortisol synthesis inhibitor ketoconazole (WO 96/04912).

Conditions related to Metabolic Syndrome include diabetes mellitus type II (IDDM), non-insulin dependent diabetes (NIDDM), myocardial infarction, stroke and other arteriosclerotic diseases as well as the risk factors for these diseases, insulin resistance in general, abdominal obesity caused by accumulation of intra-abdominal fat, elevated serum lipids, and raised diastolic and/or systolic blood pressure.

While cortisol synthesis inhibitors such as ketoconazole are a valuable means for treatment of the aforesaid conditions, there is always scope for further improvement in the prevention and treatment of the conditions generally known as or symptomatic of Metabolic Syndrome. Certain known inhibitors exhibit undesired side-effects at therapeutically effective doses and it is an aim of researchers and doctors alike to improve the efficacy of a treatment and/or lower the amount of an active ingredient which must be administered to achieve a particular effect.

The present invention accordingly seeks to provide an effective method for the prevention and treatment of the conditions commonly known as Metabolic Syndrome.

It has now been found that an effective treatment of Metabolic Syndrome and/or the symptoms or conditions associated therewith can be achieved by co-administration of a cortisol synthesis inhibitor and growth hormone.

Thus, according to one aspect, the present invention provides a method of combatting Metabolic Syndrome in a mammal, which method comprises administering a cortisol synthesis inhibitor and growth hormone to said mammal in amounts effective to combat the clinical manifestations of Metabolic Syndrome.

The term "combatting" as used herein includes both therapeutic treatment and prophylaxis (preventative treatment), and hence methods of treating and preventing Metabolic Syndrome are encompassed by the present invention.

The term "Metabolic Syndrome" is used herein to refer to the accumulation of visceral fat and the risk factors associated therewith, as well as the endocrine disturbances listed above which characterise the Syndrome. The term is also used to refer to the conditions related to Metabolic Syndrome, IDDM, NIDDM etc. as discussed above.

The steroid glucocorticoid hormone cortisol is synthesised in the adrenal glands from pregnenolone via progesterone and is itself involved in the metabolism of proteins, carbohydrates and lipids in most tissues and in the suppression of inflammatory reactions. 'Cortisol synthesis inhibitors' should be understood as agents reducing but not completely blocking the synthesis of cortisol by the human body. They are administered with the aim of reducing increased cortisol levels to normal or slightly sub-normal levels.

A large number of agents are known to suppress glucocorticoid production or inhibit their receptor binding in humans: sodium valporate (Aggernaes, H. et al. Acta Psychiatr. Scand. (1988) 77 170–174); Enkephalins and their synthetic analogues (Stubbs, W.A. et al. The Lancet (1978) 1225–1227); Opioids such as loperamide, commercially available under the trademark IMODIUM from Janssen Pharmaceutica N.V.; the antihypertensive drug Clonidine (Slowinska-Srzednicka, J. et al. European Journal of Clinical Pharmacology (1988) 35 115–121); Oxytocin (Legros, J.J. et al. Endocrinologica (1987) 114 345–349) and Mifepristone, known as RU 486 or RU 38486 available from RousselUclaf.

Any of the above agents or any of the large number of cortisol synthesis inhibitors known in the art may be used as cortisol synthesis inhibitors according to the present invention. However, the majority of known cortisol synthesis inhibitors are administered topically to fight infections by fungi; their adverse reactions and/or low absorption in the gastro-intestinal tract, in general, make them less attractive for use in the present invention. The present invention permits the oral administration of a cortisol synthesis inhibitor. Treatments and medicaments comprising the cortisol synthesis inhibitor ketoconazole were found particularly effective in the present invention by virtue, in particular, of its low toxicity and lack of other adverse effects. The particular mechanism of action of s ketoconazole results in the synthesis instead of normal cortisol of a substance known as 'crippled cortisol', which lacks the biological function of native cortisol. Derivatives of ketoconazole may also be used.

Other useful cortisol synthesis inhibitors include econazole (Squibb, U.K.) and miconazole (Janssen, Belgium) and their derivatives. Ketoconazole, econazole or miconazole in conjunction with growth hormone thus represent preferred embodiments of the present invention.

Human growth hormone is a protein having 191 amino acids and a molecular weight of 22,000 daltons and is produced in the anterior lobe of the pituitary gland or adenohypophysis. The hormone is synthesised in the form of the precursor and once processed to the active form is secreted from the cell. The mode of action of human Growth Hormone (hGH) is not well understood, but it stimulates the liver to produce somatomedin-1, which in turn causes growth of muscle and bone; stimulation of fat, muscle and cartilage cell differentiation, as well as affecting lipid and carbohydrate metabolism. Analogues of growth hormone are also known in other species, and any mammalian growth hormone (GH) or derivative thereof may be used.

Extracted and purified GH can be used in the. present invention but the use of recombinant GH (rGH) is preferred, especially recombinant human growth hormone (rhGH). Such recombination techniques are known in the art; U.S. Pat. No. 5,268,277 for example, describes a process for producing human growth hormone identical to natural human growth from a transformed *Bacillus subtilis* culture.

The term "growth hormone" includes also, in addition to native sequences, sequence- and chemicallymodified variants of the mammalian peptide, particularly the 191 amino acid hGH. All peptide fragments incorporating amino substitutions, additions and deletions to the full growth hormone are encompassed by the term, provided they retain, preferably all or substantially all, the biological activity of the native growth hormone. Assays for growth hormone activity are known in the art and could be based on the differentiation of pre-adipocytes to adipocytes [Green, H. et al., Differentiation 1985;29: 195–198]. Any recombinant growth hormone peptides should preferably have at least a 65% homology with the native peptide.

The Examples which follow give an indication of the clinically observable symptoms and conditions associated with Metabolic Syndrome which can be combatted or "treated" according to the present invention and the sort of improvements which can be expected.

More particularly, the invention provides a method of decreasing visceral fat mass associated with Metabolic Syndrome in a mammal, which method comprises administering a cortisol synthesis inhibitor and growth hormone to said mammal in an amount effective to reduce visceral fat mass.

In a further aspect, the invention provides the use of a cortisol synthesis inhibitor and growth hormone in the manufacture of a medicament for combatting Metabolic Syndrome.

In this context, "medicament" is meant in the broadest sense and is not limited to a composition which actually comprises a physical mixture of the two active ingredients. Indeed, in a preferred embodiment of the invention, the two active ingredients are not in admixture, the cortisol synthesis inhibitor being administered orally and the growth hormone subcutaneously. Additionally, "a medicament" is not limited to preparations which are administered simultaneously in a temporal sense.

In a still further aspect, the invention provides a product containing (a) a cortisol synthesis inhibitor, and (b) growth hormone as a combined preparation for simultaneous, separate or sequential use in combatting Metabolic Syndrome.

The active ingredients or agents thus need not necessarily be administered simultaneously. Separate or sequential use in the prophylactic or therapeutic treatment of Metabolic Syndrome are, in fact, preferred in the context of the present invention. Ina further aspect, the invention provides a medical product comprising a cortisol synthesis inhibitor in conjunction with growth hormone for use in combatting Metabolic Syndrome.

Alternatively viewed, this aspect of the invention also provides a kit for use in combatting Metabolic Syndrome comprising:

(a) a first container containing a cortisol synthesis inhibitor; and (b) a second container containing growth hormone.

The medical product may conveniently comrpise at least one pharmaceutically acceptable carrier or excipient.

Again, "medical product" is to be interpreted in its broadest sense and is not limited to a single entity which comprises the two active ingredients in admixture. However, an embodiment of the invention includes a pharmaceutical composition comprising both agents, together with at least one pharmaceutically acceptable carrier or excipient.

In a preferred embodiment of the invention, a pharmacologically effective amount of testosterone or one of its analogues or derivatives to compensate for reduction in testosterone levels caused by the cortisol synthesis inhibitor is also administered to the patient. Use of the combination of a cortisol synthesis inhibitor, human growth hormone, and testosterone is however only considered useful when treating male subjects.

In a further preferred embodiment of the invention, a pharmacologically effective amount of a natural or synthetic estrogen, e.g. estradiol including its analogues or derivatives, to compensate for reduction in estrogen levels caused by the cortisol synthesis inhibitor is also administered to the patient. Use of the combination of a cortisol synthesis inhibitor, human growth hormone, and a natural or synthetic estrogen is however only considered useful when treating female subjects.

'Pharmacologically effective amount' denotes a pharmacologically effective amount for each of the components in isolation, that is, an amount sufficient for giving rise to detectable levels of cortisol synthesis inhibitors in plasma and raising hGH and testosterone levels above the average levels for the individual patient, respectively.

Normal levels of cortisol in patients unaffected by metabolic Syndrome show substantial diurnal variation, with a maximum in the early morning. It has been found that for best results the cortisol synthesis inhibitors should preferably be given in the evening to cap this maximum. Average cortisol plasma levels in healthy adults are in the order of 10 $\mu$g/100 ml. Relevant data for cortisol biosynthesis in a patient are obtained through the measurement of cortisol in urine over a day, the reference interval being from about 80 to about 400 mmol per 24 h.

The active ingredients according to the present invention are: preferably administered in a time-related manner. 'Time-related manner' denotes intermittent or delayed release administration of pharmacologically effective amounts of the active agents, with substantial overlap timewise of their repetitive (or delayed release) administration. In other words, while the cortisol synthesis inhibitor (or at least part of the daily dose) is preferably administered in the evening, around bedtime, the growth hormone should preferably be administered in the morning. If a sex hormone is also to be administered, this should preferably be with patches which provide a fairly constant release of the hormone during the day. However, other "timed" administration regimes may be followed, which may be determined by the physician or prescribing practitioner according to clinical need or as desired according to routine medical practice and techniques known in the art.

The cortisol synthesis inhibitor and the growth hormone are preferably administered daily over at least 80% of the administration period. The sex hormone is preferably administered daily over at least 50% of the administration period.

Such a regime of administration is preferably maintained for at least one month, more preferably 6 months or longer. A successful course of treatment is characterised, inter alia, by a reduction in visceral fat mass, a lowering of blood pressure, an increase in insulin sensitivity, a reduction in fasting blood glucose levels and a reduction in serum cholesterol and triglyceride levels.

The medicaments and compositions according to the invention can be formulated in a conventional manner, in admixture with pharmaceutically acceptable, inert diluents, carriers and/or excipients. Suitable formulations are discussed in the Examples. hGH formulations may be lyophilised in order to obtain a dry powder or in liquid form for immediate use. WO 9535116 describes formulations for hGH which comprise saccharose and are particularly effective for formulations which contain recombinant human growth hormone. Any of the above could be used in accordance with the teaching of the present invention. Formulations may comprise between 1 and 99% of active ingredients. If desired, the cortisol synthesis inhibitor composition may contain a mixture of such inhibitors. The active agents or compositions may thus be formulated as tablets, pills, capsules, suppositories, pessaries and the like or as solutions, suspensions, creams, pastes, gels, implants, transdermal patches etc. or any other means.

As mentioned above, the active agents may be formulated together or, more preferably, separately. Any of the available administration forms may be used, and the active agents may, for example, each be administered enterally (e.g. orally or rectally), parenterally (e.g. intravenously, intramuscularly or is sub-cutaneously), topically (including transmucosally and transdermally) or by any other means.

While the cortisol synthesis inhibitor is preferably administered orally, the sex hormone is preferably administered transdermally, e.g. via a patch or by intramuscular injection, preferably of microcapsules or via a device for implantation and the growth hormone is preferably administered by subcutaneous injection.

The invention will now be described in more detail in the following non-limiting Examples.

EXAMPLE 1

A. Administration of Ketoconazole

Ketoconazole (cis-1-acetyl-4-[4-[[2-2(2,4-dichlorophenyl)-2-(1H-imidazol-ylmethyl)-1,3-dioxolan-4-yl]-methoxy]phenyl]piperazine; U.S. Pat. Nos. 4,144,346 and 4,223,036; tablets containing 200 mg ketoconazole are manufactured by Janssen (Belgium) and marketed under the trademark Fungoral®. Administration (adults) 1–4 tablets/day (the preferred range is from about 50 mg to about 1 g/day), at least 50% of the daily dosage preferably given at bedtime.

B. Administration of Growth Hormone

Recombinant human growth hormone (somatropin) manufactured by Novo Nordisk (Denmark) and marketed under the trademark Norditropin®. Liquid for injection 12 IE (I+II)/ml. Administered by subcutaneous or intramuscular injection; 0.2–2 ml of this solution given once a day.

C. Administration of Testosterone

Testosterone enanthate 250 mg/ml in benzyl benzoate/castor oil; manufactured by Schering AG (Germany)and marketed under the trademark Testoviron® Depot. Administered by intramuscular injection in intervals of about 3 weeks. Preferred single dosages are 0.2–1.0 ml. Alternative administration is by patches releasing about 2.5 mg/day, marketed under the trademark Atmos® by AB Astra (Sweden). Preferred administration of 1–3 patches/day (2–10 mg testosterone per 24 h).

D. Administration of Estradiol

Patches releasing 24 µg 17β-estradiol (Estraderm®, Ciba) over 24 h applied in a number sufficient for compensating the decrease in estrogen levels.

EXAMPLE 2

Observations on Three Patients

The patients (2 men, aged 47 and 62 years; 1 woman, aged 57 years) were moderately to very overweight with pronounced visceral adiposity. All showed moderately elevated blood pressure and reduced insulin sensitivity. Administration (for medicaments, see above): ketoconazole, 2–3 tablets/day, of which one or two at bedtime; hGH 0.15–0.20 IU/kg body weight, subcutaneously once a day (usually in the morning); testosterone 2 or 3 patches per day.

During the first 6–8 weeks of treatment visceral fat mass decreased slowly; no other clinical signs were observed during that period. During the next phase, up to 9–12 months from start, visceral fat was seen to decrease further, the total decrease being from about 20% to 30% (typically, from about 8 to about 5.5 kg) as measured by computerised tomography (CT). Systolic blood pressure decreased from 180 to 165 mm Hg and diastolic blood pressure from 92 to 84 mm Hg. Insulin sensitivity, as measured by the clamp method increased by about 45%, on average (from 2–4 to 3–8 mg glucose/L). Fasting blood glucose decreased by about 0.5 to 1.0 mmol/L, for instance from 5.8 to 5.0 mmol/L in a patient without diabetes, and from 9–6.5 in a patient with manifest diabetes. Total serum cholesterol decreased from 7.8 to 5.9 mmol/L; serum triglycerides decreased from 2.7 to 1.9 mmol/L. The patients also experienced an improvement of their physical and mental health status.

EXAMPLE 3

Two women and two men were treated with a cortisol inhibitor (ketoconazole at a dose of 400 mg) and growth hormone in the dose of 0.15 IU/kg body weight. All patients were abdominally obese, one man and one woman also had overt diabetes. In summary, they all had signs of Metabolic Syndrome. After 8 months, all patients were found to be improved regarding the following parameters:

Patient 1 (male, 58 years old)

|  | Before | After |
| --- | --- | --- |
| Fasting glucose | 6.3 mmol/l | 5.7 mmol/l |
| Systolic blood pressure | 187 mm Hg | 176 mm Hg |
| Diastolic blood pressure | 102 mm Hg | 97 mm Hg |
| Insulin sensitivity (as measured by the clamp method described) | 5.4 mg glucose/kg/ min | 6.4 mg glucose/kg/ min |
| Fasting Cholesterol/S* | 8.3 mmol/l | 7.5 mmol/l |

Patient 2 (male, 62 years old)

|  | Before | After |
| --- | --- | --- |
| Fasting glucose | 5.3 mmol/l | 5.0 mmol/l |
| Systolic blood pressure | 173 mm Hg | 169 mm Hg |
| Diastolic blood pressure | 97 mm Hg | 92 mm Hg |
| Insulin sensitivity (as measured by the clamp method described) | 6.5 mg glucose/kg/ min | 7.5 mg glucose/kg/ min |
| Fasting Cholesterol/S | 7.9 mmol/l | 7.5 mmol/l |

Patient 3 (female, 64 years old)

|  | Before | After |
| --- | --- | --- |
| Fasting glucose | 5.9 mmol/l | 5.2 mmol/l |
| Systolic blood pressure | 164 mm Hg | 159 mm Hg |
| Diastolic blood pressure | 90 mm Hg | 86 mm Hg |
| Insulin sensitivity (as measured by the clamp method described) | 4.8 mg glucose/kg/ min | 5.9 mg glucose/kg/ min |
| Fasting Cholesterol/S | 6.9 mmol/l | 6.2 mmol/l |

Patient 4 (female, 67 years old)

|  | Before | After |
| --- | --- | --- |
| Fasting glucose | 5.2 mmol/l | 4.9 mmol/l |
| Systolic blood pressure | 171 mm Hg | 162 mm Hg |
| Diastolic blood pressure | 89 mm Hg | 85 mm Hg |
| Insulin sensitivity (as measured by the clamp method described) | 6.8 mg glucose/kg/ min | 7.9 mg glucose/kg/ min |
| Fasting Cholesterol/S | 6.5 mmol/l | 6.0 mmol/l |

In addition patient 1, 2 and 4 reported improvements of their physical and mental health status.

After 8 months, testosterone treatment was added to the treatment regime, with the aim of restoring testosterone levels to normal values in the men and they improved further having regard to the above parameters. The other treatments were unchanged. Also, for the women, estrogen treatment was added and they were moderately further improved having regard to the above mentioned parameters.

Finally, it was observed that the liver transaminases of all patients had decreased by about 35–40%, indicating a reduced liver steatosis.

I claim:

1. A method of treating or preventing metabolic syndrome in a mammal, which method comprises administering a cortisol synthesis inhibitor and growth hormone to said mammal in an amount effective to treat or prevent the clinical manifestations of metabolic syndrome.

2. A method of decreasing visceral fat mass associated with metabolic syndrome in a mammal, which method comprises administering a cortisol synthesis inhibitor and growth hormone to said mammal in an amount effective to reduce said visceral fat mass.

3. A medical product comprising (a) a cortisol synthesis inhibitor, and (b) growth hormone, as a combined preparation for simultaneous, separate or sequential use in treating or preventing metabolic syndrome or for decreasing visceral fat mass associated with metabolic syndrome.

4. The method according to claim 1 wherein the cortisol synthesis inhibitor is selected from the group consisting of ketoconazole, econazole and miconazole or a derivative thereof.

5. The method according to claim 2 wherein the cortisol synthesis inhibitor is selected from the group consisting of ketoconazole, econazol and miconazole or a derivative thereof.

6. The medical product according to claim 3 wherein the cortisol synthesis inhibitor is selected from the group consisting of ketocanazole, econazol and miconazole or a derivative thereof.

7. The method according to claim 4 or 5 wherein the cortisol synthesis inhibitor is ketoconazole.

8. The medical product according to claim 6 wherein the cortisol synthesis inhibitor is ketoconazole.

9. The method according to claim 4 or 5 further comprising the administration of a sex hormone selected from testosterone and a natural or synthetic estrogen.

10. The medical product according to claim 6 further comprising a sex hormone selected from testosterone and a natural or synthetic estrogen.

11. The method according to claim 4 or 5 wherein the administration extends over a period of a month or more.

12. The method according to claim 4 or 5 wherein the cortisol synthesis inhibitor and the growth hormone are administered daily for at least 80% of the administration period.

13. The method according to claim 4 or 5 wherein the sex hormone is administered by a controlled release formulation which releases pharmacologically effective amounts of the sex hormone over at least 50% of the administration period.

14. The method according to claim 4 or 5 wherein the cortisol synthesis inhibitor and growth hormone are administered in a time-related manner.

15. The method according to claim 14 wherein the cortisol synthesis inhibitor is administered to the patient in the evening and the growth hormone is administered in the morning.

16. The method according to claim 14 wherein the cortisol synthesis inhibitor is administered to the patient at least 7 hours after the growth hormone in any given day.

17. The method according to claim 16 wherein the cortisol synthesis inhibitor is administered at least 10 hours after the growth hormone.

18. A kit for use in treating or preventing metabolic syndrome comprising:
   (a) a first container comprising a cortisol synthesis inhibitor; and
   (b) a second container comprising growth hormone.

* * * * *